United States Patent [19]

Weiss

[11] 4,104,531
[45] * Aug. 1, 1978

[54] ELECTRON BEAM TARGET CARRIER WITH CERAMIC WINDOW FOR DENTAL OR MEDICAL X-RAY USE

[75] Inventor: Mortimer E. Weiss, Laguna Beach, Calif.

[73] Assignee: Thoro-Ray Inc., Fort Worth, Tex.

[*] Notice: The portion of the term of this patent subsequent to Aug. 1, 1995, has been disclaimed.

[21] Appl. No.: 777,133

[22] Filed: Mar. 14, 1977

Related U.S. Application Data

[63] Continuation-in-part of Ser. No. 728,959, Oct. 4, 1976, which is a continuation-in-part of Ser. No. 672,608, Apr. 1, 1976, abandoned.

[51] Int. Cl.² ..................... H01J 35/00; H05G 1/00
[52] U.S. Cl. ................... 250/490; 250/439 P; 250/515
[58] Field of Search ............ 250/404, 439 P, 510, 250/399, 490, 505, 515

[56] References Cited

U.S. PATENT DOCUMENTS

| | | | |
|---|---|---|---|
| 1,881,448 | 10/1932 | Forde et al. | 250/399 |
| 2,531,583 | 11/1950 | Ott | 250/404 |
| 2,946,892 | 7/1960 | Bas-Tagmaz | 250/404 |
| 3,906,235 | 9/1975 | Fischer | 250/404 |

Primary Examiner—Alfred E. Smith
Assistant Examiner—B. C. Anderson
Attorney, Agent, or Firm—William W. Haefliger

[57] ABSTRACT

Dental X-ray apparatus characterized by very substantial reductions in radiation exposure of the patient, incorporates a ceramic window in a probe receivable into a patient's mouth, and comprises:

a. X-ray tube means for providing an electron beam,
b. a target for said beam, and
c. a carrier for said target and locating the target in longitudinally spaced relation from said means to be received rearwardly into a patient's mouth,
d. said carrier defining a tubular X-ray shield, and there being a ceramic element defining an X-ray window carried by the carrier and positioned to sidewardly laterally pass X-rays emanating from the target.

17 Claims, 27 Drawing Figures

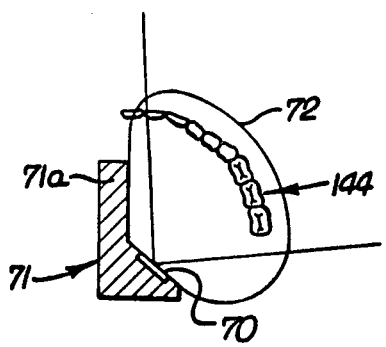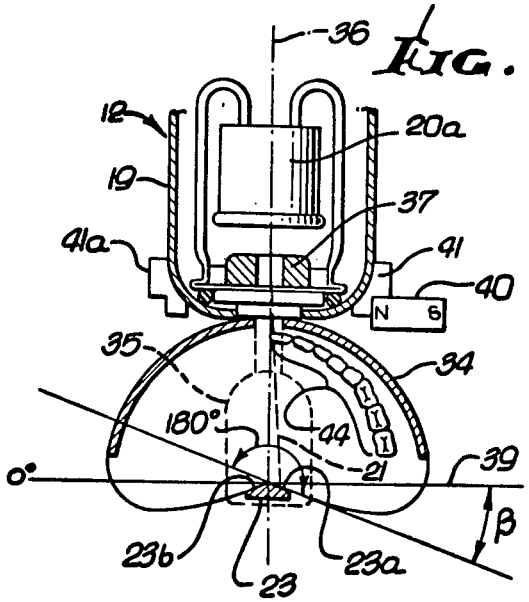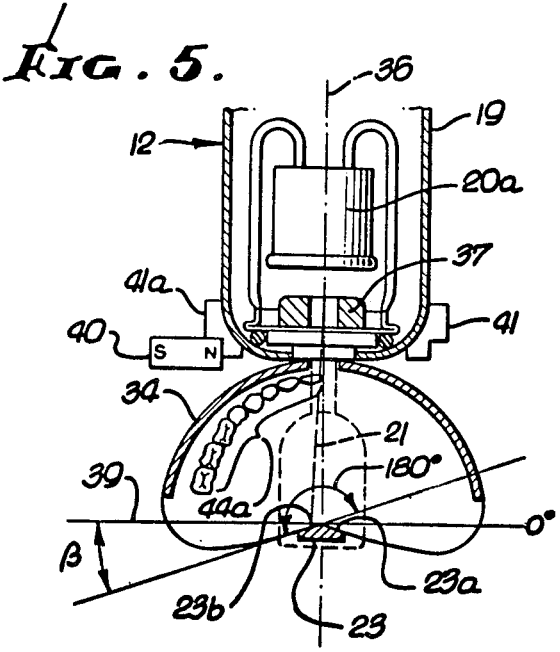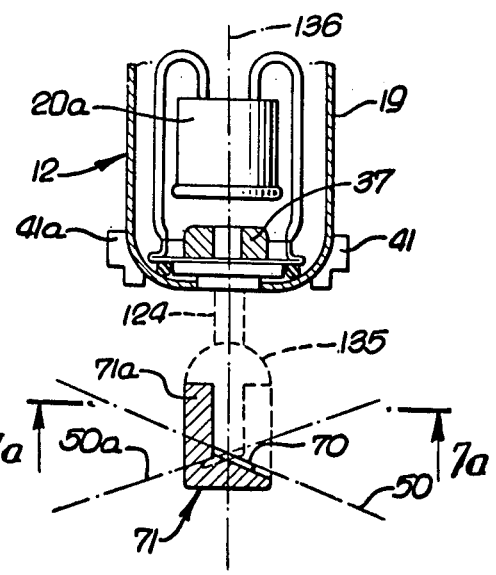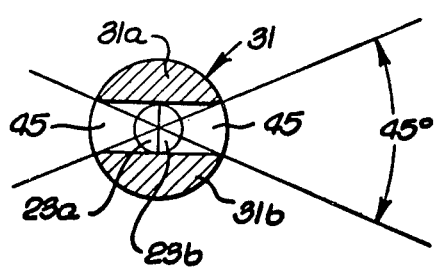

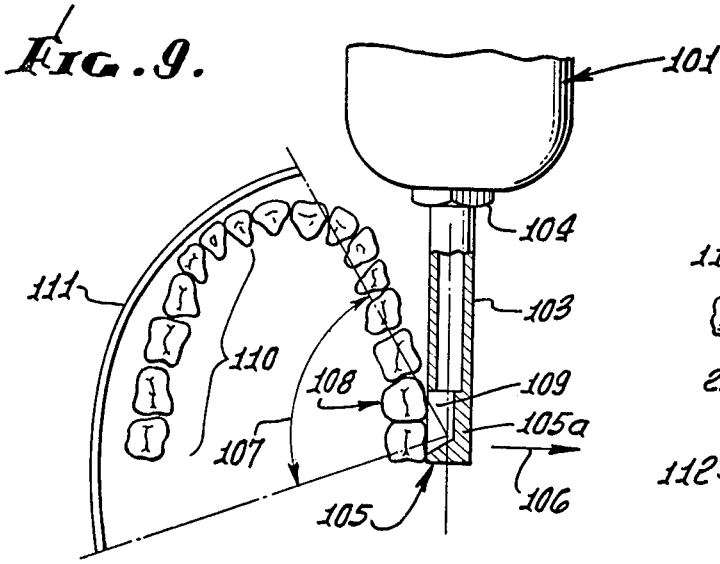
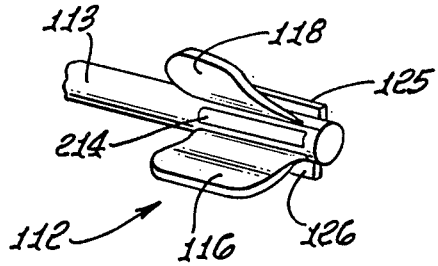
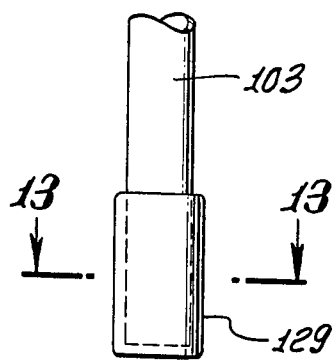
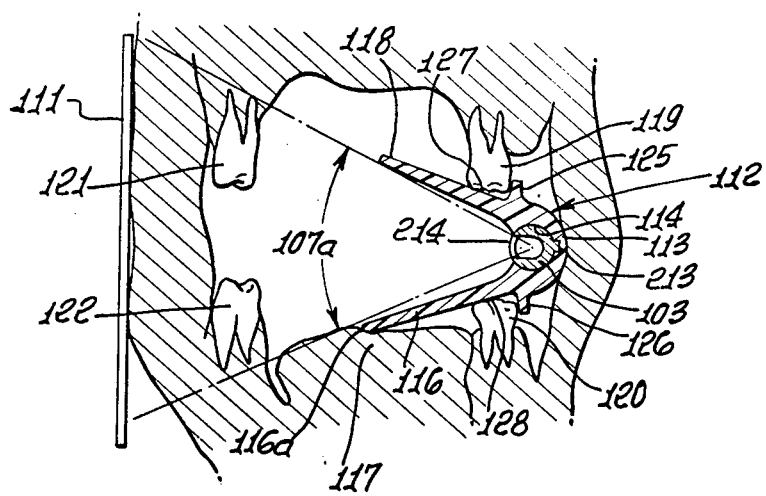
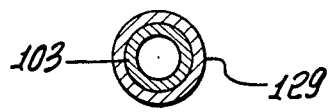

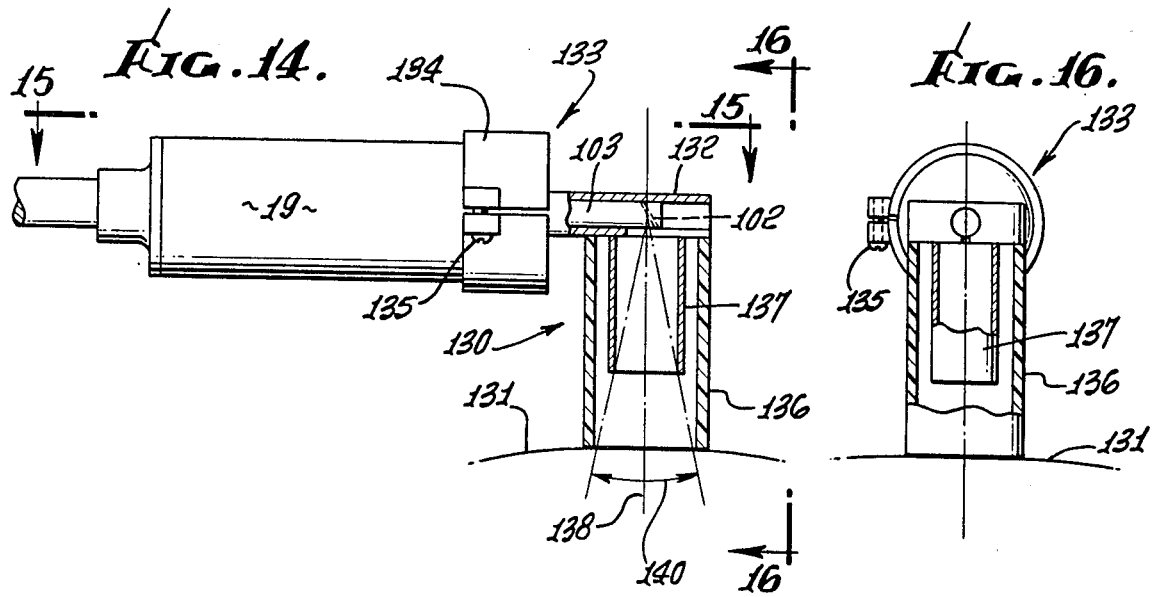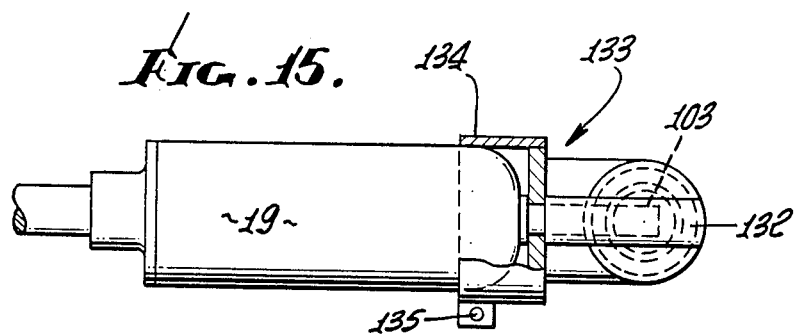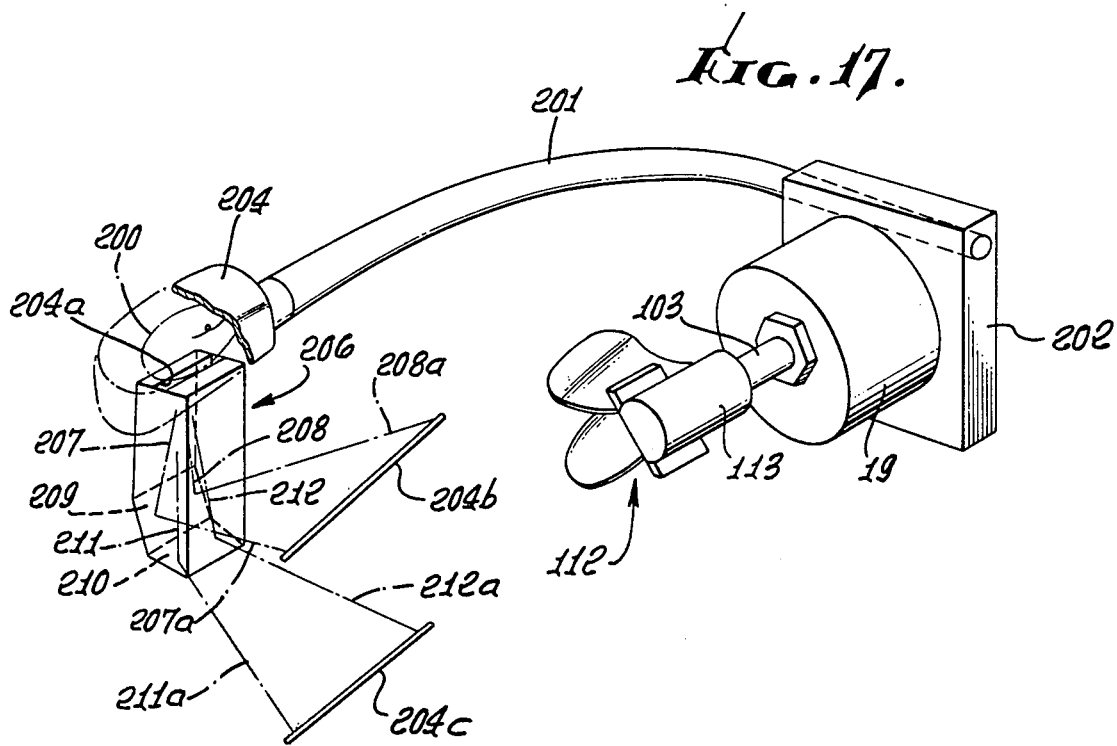

ELECTRON BEAM TARGET CARRIER WITH CERAMIC WINDOW FOR DENTAL OR MEDICAL X-RAY USE

BACKGROUND OF THE INVENTION

This application is a continuation-in-part of my application Ser. No. 728,959, filed Oct. 4, 1976, and which was a continuation-in-part of my earlier application Ser. No. 672,608, filed Apr. 1, 1976 and entitled "Dental and Medical X-ray Apparatus" now abandoned.

This invention relates generally to X-ray apparatus and techniques; more particularly, it concerns method and equipment enabling rapid X-ray examination of teeth, with substantially reduced exposure to radiation.

Present systems of X-ray examination of human teeth require twelve to fourteen exposures, accompanied by objectionably excessive amounts of side radiation to sensitive areas of the brain, cortex, sinus, throat, optic and auditory nerve centers. Recently, a technique has been proposed according to which an X-ray target is introduced into the mouth, and radiation is directed from the target back through the teeth to film supported outside the mouth, thereby to produce a so-called high resolution, panoramic radiograph. One problem encountered with that type equipment concerns the tendency to produce gagging of the patient, due to the necessity of locating the target sufficiently close to the throat that back teeth will be exposed to produced X-rays. Another problem has to do with the requirement that the upper and lower teeth be alternately exposed to radiation, which in turn requires that the shield associated with the target be re-arranged. This means that the target is removed from the oral cavity after the first exposure (as for example irradiation of the upper teeth, after which the target is re-introduced to enable the second exposure (of the lower teeth) which increases the risk of gagging and otherwise discomforts the patient.

SUMMARY OF THE INVENTION

It is a major object of the invention to provide improvements in technique and apparatus which will overcome the above objects and disadvantages. Another object is to provide intra-oral X-ray equipment wherein a ceramic window is provided in a tubular carrier for passing X-rays, and in such manner that improved, higher clarity tooth images will be produced on film.

Basically, the invention is embodied in apparatus that includes:
  a. X-ray tube means for providing an electron beam,
  b. a target for said beam, and
  c. a carrier for said target and locating the target in longitudinally spaced relation from said means to be received rearwardly into a patient's mouth,
  d. said carrier defining a tubular X-ray shield, and there being a ceramic element defining an X-ray window carried by the carrier and positioned to sidewardly laterally pass X-rays emanating from the target.

As will be seen, the window cooperates with the X-ray shield defined by the carrier, and in one form of the invention the window and shield are tubular and coaxial. In addition, an auxiliary semicylindrical X-ray shield may be located to extend around the ceramic element and to define certain boundaries for X-rays passing through the window. Another such boundary may be defined by a sleeve extending about and positioning a portion of the ceramic element and carrier.

A further important object of the invention is to provide a ceramic window cooperating with an X-ray shielding and tongue suppressor means carried to be received into the patient's mouth, and characterized in that when the target is located at one side of the mouth to direct an X-ray beam passing through the ceramic window and toward teeth at the opposite side of the mouth, the shielding and tongue suppressor means will protect portions of the head from the X-ray beam and the patient's tongue will be suppressed relative to the X-ray beam. As will appear, the apparatus may include a tubular carrier for the target projecting rearwardly of the X-ray tube itself, and the shielding and tongue suppressor means may advantageously comprise a component having a base defining an opening removably receiving the tubular carrier and ceramic element; further, that component may have arms which project sidewardly of the base with V-shaped configuration, the lower arm extending sufficiently downwardly and sidewardly as to suppress the patient's tongue when the base is received between the patient's upper and lower molars. In this regard, the referenced component may consist of plastic material containing X-ray shielding substance, as for example barium; and it may carry upper and lower projections to fit adjacent the outer-sides of the patient's upper and lower molars for positioning purposes, and so that the molars may clench the component to position it for tongue suppression and shielding orientation relative to the mouth and head of the patient; also a longer source to film distance is enabled.

These and other objects and advantages of the invention, as well as the details of illustrative embodiments, will be more fully understood from the following description and drawings in which:

DRAWING DESCRIPTION

FIGS. 4 and 5 are top plan views of gun and target relationships, in schematic form;

FIG. 6 is an enlarged frontal view of the target and shield;

FIG. 7 is a view like FIG. 4 in FIG. 5, but showing an alternative target; and FIG. 8 shows another target;

FIG. 7a is a section taken on lines 7a—7a of FIG. 7;

FIG. 9 is a view like FIG. 5, showing modified apparatus wherein the target is located at one side of the patient's mouth;

FIG. 10 is a perspective view of an X-ray shield and tube positioning tongue suppressor attachment;

FIG. 11 is a vertical section taken through a patient's mouth showing use of the FIG. 10 attachment in conjunction with an X-ray tube, target and carrier as for example is shown in FIG. 9;

FIG. 12 is a plan view of a carrier for an X-ray producing target, and showing a filter on the carrier;

FIG. 13 is a cross-section taken on lines 13—13 of FIG. 12;

FIG. 14 is a side elevation showing an attachment for the FIG. 9 apparatus, enabling its use externally of the patient's mouth;

FIG. 15 is a plan view taken on lines 15—15 of FIG. 14;

FIG. 16 is an elevation taken on lines 16—16 of FIG. 14;

FIG. 17 is a perspective view of means to delineate a head zone to be irradiated;

DETAILED DESCRIPTION

Figure 1:
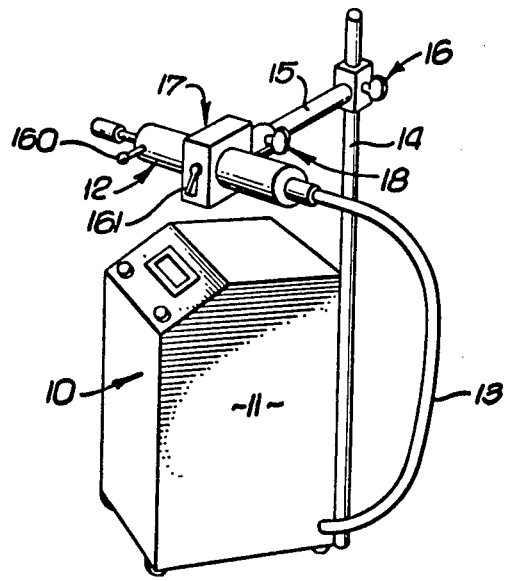
FIG. 1 is a perspective showing of high voltage generator equipment and X-ray tube mobile or floor mount associated with the invention.

Referring first to FIG. 1, X-ray apparatus 10 includes a high voltage generator console 11 to which X-ray tube 12 is electrically connected, as via cable 13. A suitable adjustable support for the tube 12 includes upright post 14 carried by the console; an arm 15 adjustably attached at 16 to the post to rotate about a vertical axis; and a mount 17 for the tube apparatus and adjustably attached at 18 to the arm 15 to rotate or swivel about a horizontal axis.

Figure 2:
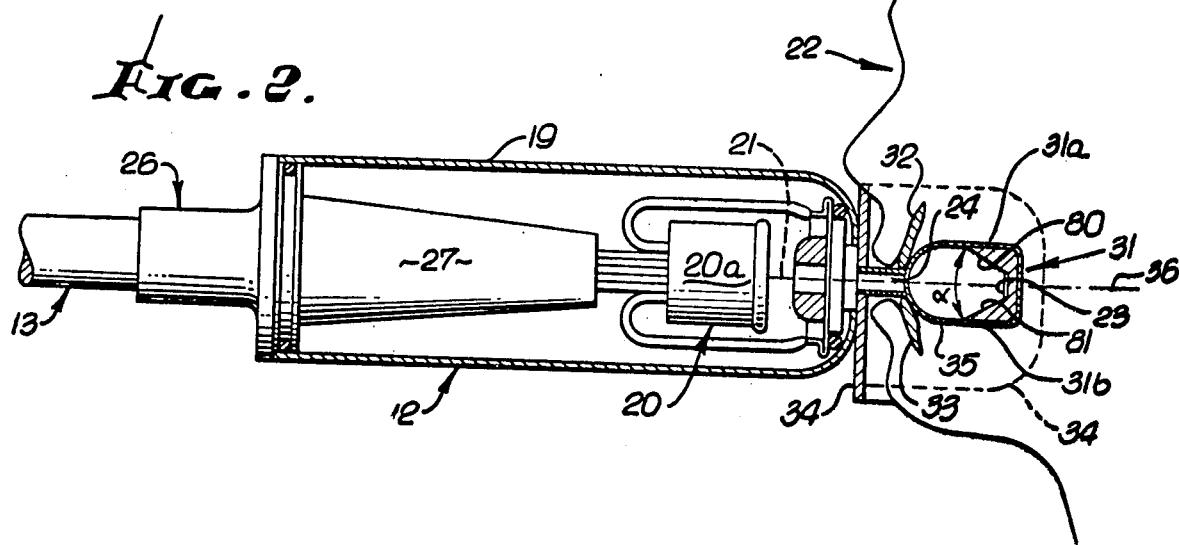
FIG. 2 is a cross sectional view of gun and target apparatus embodying the invention.

Extending the description to FIG. 2, the tube means 12 includes a housing 19 containing the micro-focus X-ray tube 20 which produces an electron beam 21. A beam target 23 is carried by the tube means and is located axially rearwardly thereof (relative to the patient's head 22) to be inserted or received relatively rearwardly into the patient's mouth. The forward and rearward axis appears at 36. In the example shown, the target 23 is carried by the rearward end portion of a rearwardly axially elongated tubular element 24 projecting into the patient's mouth. The cable 13 is attached to the housing at 26, and passes through an insulator 27 to the gun 20a. The inner conductor of the cable is at high potential while the outer cable sheath is at ground potential and is solidly connected to the tube housing. The tube anode is also at ground potential and only the electron gun 20a is at high potential, insulated by gas or oil inside the tube housing. This provides the necessary electrically shock-proof mounting for intraoral radiography.

Figure 3:
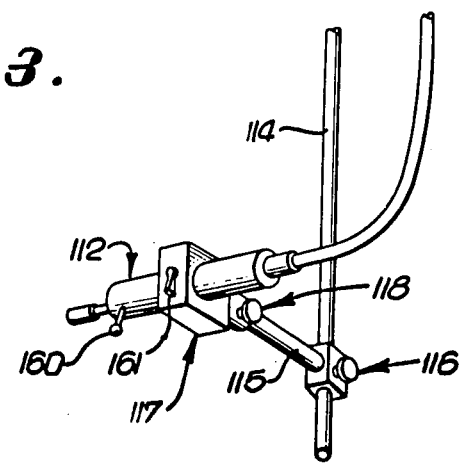
FIG. 3 is a perspective showing of an alternative X-ray tube ceiling or wall mounting.

An alternative ceiling mount for the tube 112 in FIG. 3 includes an upright post 114 affixed to or carried by the ceiling of a room. Elements 115–118 correspond to elements 15–18 in FIG. 1.

The target 23 may consist of tungsten embedded in a copper shield 31, the latter having upper and lower rearwardly tapering surfaces 80 and 81 which define an angle α therebetween. That angle subtends a zone which encompasses the patient's upper and lower teeth (including root areas) indicated at 32 and 33, but not including the brain or sinus area, the latter as well as the throat being protected from radiation impingement. In this regard, an X-ray film holder 34 is carried by the apparatus 12 to extend at the front of the patient's mouth, and to overlap his cheeks at opposite sides of the mouth. The film holder is also substantially subtended by the angle α. Alternatively, the film may be held in place against the patient's face as by an elastic strap wrapped around his head, or the strap may incorporate VELCRO holding means. The target and shield are carried by the anode envelope 35 which is in turn carried by the tubular element 24. The anode envelope material is a low X-ray absorbtion material such as beryllium, titanium, aluminum, aluminum oxide and beryllium oxide and forms the window for radiation emission.

Extending the description to FIG. 4, the tube anode 37 is shown axially rearwardly of the gun 20a. The target 23, located axially rearwardly of the anode, has surfaces 23a and 23b angled rearwardly and transversely (i.e. sidewardly) relative to the axis 36. Surfaces 23a and 23b are transversely symmetrical relative to axis 36, and taper axially forwardly, as shown, at angles β relative to an upright plane 39 normal to axis 36; angle β may for example be about 20°.

In accordance with an important aspect of the invention, means is provided to effect transverse shifting of the radiation pattern produced in response to beam incidence on the target. Such means may comprise a magnet supported to be shifted transversely to deflect the beam transversely relative to the target; for example, FIG. 4 shows the magnet 40 suitably supported at 41 by the tube at the right side of the axis 36, and rearwardly of the anode 37, the magnet acting to deflect the beam 21 transversely rightwardly so that it impinges on surface 23a. As a result, X-rays are produced to travel forwardly through the upper and lower teeth at the right side of the patient's mouth and to the film in holder 34, such teeth indicated at 44. Actually, radiation may extend transversely over the 180° angle indicated, and defined by the plane of surface 23a, and the shield does not interrupt such sideward radiation. See in this regard the shield openings 45 at opposite sides of the target, in FIG. 6. Accordingly, the shield has sections 31a and 31b above and below the target.

Upon completion of exposure of the right side teeth 44 to X-radiation, the magnet 40 is transversely shifted to the left side of axis 36, i.e. to a position as for example appears in FIG. 5. In that position, suitably supported at 41a by the tube, the magnet acts to deflect the beam 21 transversely leftwardly, so that it impinges on target left surface 23b. As a result, X-rays are produced to travel forwardly through the patient's upper and lower teeth at the left side of the mouth, and to the film in the holder 34, such teeth indicated at 44a. Here again, radiation may extend transversely over the 180° angle indicated and defined by the plane of surface 23b. The shield does not interrupt such sideward radiation, but does limit radiation in upper and lower directions, to remain within the angle α previously described.

Holders 41 and 41a may suitably releasably retain the magnet, as by detents. If desired, the magnet 40 may be rotatably carried to swing about axis 36 between the positions seen in FIGS. 4 and 5.

FIG. 7 shows an alternative means to effect transverse shifting of the X-ray pattern with a fixed target, seen in FIG. 8. In this view, the tube 12 and supported target 70 are rotatable about axis 136 between the solid line and broken line target surface positions shown at 50 and 50a. For example, in FIG. 1 the mount 17 may incorporate means rotatably support the tube 12 to rotate about axis 136. A sidewardly projecting handle to rotate the tube 180° outside the mouth appears at 160. A tube position locking toggle appears at 161. In target position 50, the operation corresponds to that described in FIG. 4; whereas in target position 50a, the operation corresponds to that described in connection with FIG. 5. Envelope 135 and support element 124 correspond to items 35 and 24 in FIG. 2.

FIG. 8 shows the modified tungsten target 70 supported by shield 71, the latter projecting forwardly at 71a sidewardly of the target to block X-ray sideward travel and confine same to the region 72. The latter is related to teeth 144 at one side of the mouth, as shown. Portions of the copper shield 71 not shown extend above and below the target and forwardly as in FIG. 6, so that a side opening is formed at only one side of the target. Target 70 and shield 71 rotate with the tube, as explained above.

Finally, it should be pointed out that since the X-ray intensity necessary for the required film density is proportional to the square of the focus-to-film distance, the radiation output of the X-ray source at 5cm need be only 1/25 or 4% of that required at 25cm with the conventional extra-oral X-ray tube distance.

The wide-angle radiation pattern of the present tube can expose a panoramic view of half the mouth including upper and lower teeth in one exposure, so that only two X-ray pictures are necessary instead of 12 with conventional extra-oral tubes. When this correction 1/6 is included in the 4% noted above, the total reduction in radiation amounts to only 0.66% of that required with conventional dental radiography for the same visual information. This is a very significant reduction in radiation dosage which is less than 1% of the present radiation level for whole-mouth dental radiography.

Referring to FIG. 9, the modified apparatus 100 includes an X-ray tube means 101, and a target 102 spaced from the tube to be received rearwardly into a patient's mouth. A tubular carrier element 103 for the target is attached to the tube means as at 104 and projects rearwardly. The target may be supported by a shield 105 similar to shield 71 described above. It is carried by the carrier tube 103 and projects forwardly at 105a sidewardly of the target to block X-ray sideward travel in the direction 106 and confine X-ray travel to the region designated at 107. The latter is related to teeth 108 at one side of the mouth, as shown. Portions of the shield extend above and below the target (as in FIG. 7a) and forwardly of the target as at 105h, so that a side opening is formed at only one side of the target. The target and shield rotate with the carrier probe or tube 103, and a window 109 is formed in the latter to pass X-rays. With the 30° target oriented as shown, and between upper and lower molars at one side of the mouth, the sidewardly directed wide angle X-ray beam at 107 traverses all the upper and lower teeth 110 at the opposite side of the mouth, a film 111 being located outside or inside the mouth and proximate teeth 110 for exposure to the X-radiation and recordation of tooth and gum images. Accordingly, only two exposures are needed to record images of all teeth, one exposure as illustrated, and an opposite side (mirror image) exposure with the target located proximate the molars at the opposite side of the mouth and directing X-rays rightwardly.

Referring to FIGS. 10 and 11, the elements 100–105 and 109 remain as in FIG. 9; however, additional and very important structure is provided, namely, X-ray shielding and tongue suppressor means carried by the apparatus to be received into the patient's mouth and characterized in that when the target is located at one side of the mouth to direct an X-ray beam toward teeth at the opposite side of the mouth the shield will protect portions of the mouth from the X-ray beam and the patient's tongue will be suppressed relative to the X-ray beam. While such apparatus may take various forms, that form as illustrated by component 112 in FIGS. 10 and 11 is of unusual advantage. It includes a base 113 which is rearwardly lengthwise elongated and forms an elongated opening or semi-circular bore 114 sized to snugly receive the tube 103, i.e. with frictional or other (such as tongue and groove at 213) interfit resisting relative rotation of the component 112 and tube 103. Preferably, the component 112 has removable attachment to the tube 103, for ready replacement by another component for use with a different patient. Thus, component 112 may be dispensible, and provides a new, sterile hygienic cover for the tube 103 for each use. Tube 103 may consist of copper or Monel, and have a titanium window 214 to pass radiation.

The component 112 also typically includes arms projecting sidewardly from the C-shaped base 113 with V-shaped relative configuration, the radiation passing between the arms. As illustrated, the lower arm 116 extends downwardly and sidewardly sufficiently to extend centrally over the patient's tongue 117 to forcibly suppress same out of the main path of the radiation beam, the vertical path of which may sweep an arc such as at 107a in FIG. 11. Note the edge 116a of arm 116 over the center of the tongue, with base 113 clenched between the patient's upper and lower molars 119 and 120 at one side of the mouth (the right side, as also related to FIG. 9). Therefore, component 112 also acts to position tube 103. The upper arm 118 typically extends upwardly and sidewarldly toward the root area of the upper molars 121 at the opposite side of the mouth, and in this regard, arm 116 typically extends toward the root area of molars 122. The two arms also function as shields to prevent X-ray travel outside the path or arc 107a, i.e. protecting the palate and below tongue areas of the head, containing sensitive gland, sinus and brain zones. The X-ray paths 107 and 107a may include the temporo-mandibular joint.

The component 112 may advantageously consist of plastic material (such as polyethylene) containing X-ray shielding material, as for example barium particles dispersed throughout the plastic in as-molded or formed condition. Other shield substances and component compositions may be utilized. Coning of the beam to enhance the radiograph is also provided by component 112 including arms 116 and 118; i.e. beam "scatter" is reduced or eliminated.

In the mode of use as illustrated in FIGS. 9 and 11, with a substantially longer source-to-image distance than is characteristic of FIG. 4 use, the magnification, distortion and geometric unsharpness are all reduced to improve the overall resolution of the X-ray beam.

FIG. 11 also illustrates the provision of upper and lower integral projections or tabs 125 and 126 on the component 112, to engage the outersides of the posterior molars as shown. They aid in positioning the component relative to the molars when the patient bites down into the outer surfaces 127 and 128 of the component. Pockets are formed between the lengthwise extending tabs 125 and 126 and arms 116 and 118, to receive and locate the molars, during bite-down, firmly locating the arms 116 and 118.

FIGS. 12 and 13 show the provision of an additional X-ray filter 129 extending over the tube 103. Tubular filter 129 may consist of aluminum or other shielding material. The filter may form a window to register with window 109.

FIGS. 14–16 illustrate the use of an extra-oral source adapter removably carried by the tube 103. The adapter structure 130 typically projects sidwardly of the carrier tube 103 and target 102, and is located to pass an X-ray beam sidewardly from the target toward a patient's anatomy, and exteriorly thereof. For example, the structure may be placed against the cheek area 131 adjacent the teeth, the X-ray film then being located inside the mouth in a conventional manner. The structure 130 may include a support cylinder 132 removably slipped onto or over the tube 103, and suitably secured to the X-ray tube housing, as at 133. The latter may include a bracket 134 which encompasses the housing 19 and may be clamped thereto as by tightening screw 135.

The structure 130 includes beam collimator means defined by plastic cylinder 136 and internal metallic tubular shield 137. These elements extend generally coaxially with respect to the axis 138 of the X-ray beam embraced by arc 140. Element 136 projects further from the cylinder 132 than element 137, and both tend to limit the beam to a narrow cone circumscribing the rectangular periapical X-ray film used in conventional extra-oral radiography.

Among the advantages of the above apparatus are the following:

1. Increased magnification of the tooth area facilitates diagnosis; for example, detection of pulp in the root area is made easier, and the results of grinding of teeth show up more clearly. Thus, the dentist can more accurately inform the patient of grinding and the deleterious results of same including possible injury to the jaw hings joint. Splintering of teeth is also more easily detectable, and sinus areas can be X-rayed to show up more clearly.

2. The depression of the tongue prevents obscuration of the film.

3. The probe is positioned by the component 112 for obtaining a properly aligned radiograph, eliminating need for repetitive re-taking of radiographs, eliminating aggravation and irritability of a patient. Coning of the beam is also achieved, to enhance the radiograph.

4. The side-to-side interior X-ray technique enabled by the invention facilitates rapid taking of full mouth X-rays, using only two exposures, which in turn facilitates accurate charting of teeth by the dentist. Also, the patient can be shown the full X-ray picture, and can easily see what dental work needs to be done, so that communication between dentist and patient is improved.

5. The invention used for panoramic radiographs reduces need for conventional bite-wings and their holders inserted into the mouth, obviating discomfort and injury that can result from these items.

6. The probe itself (target and carrier) can be used in emergencies such as accidents wherein patients undergo severe facial injury, so as to secure pictures of the extent of that injury. Also, information highly useful for plastic surgery can be easily obtained.

7. Irradiation of sensitive areas of the brain, optic nerve, thalmus and thyroid glands is avoided.

8. Full X-ray data, obtainable through use of the invention, is easily obtained for use as best evidence in legal proceedings.

Finally, FIG. 17 illustrates the provision of a support operatively connected to the above described X-ray tube means, together with other means carried by the support at a location to project toward the patient's head an image delineating an area within the main path of the X-ray beam. As illustrated, such other means typically includes a light source 200 carried by the support arm 201, the latter extending from a mount 202 attached to the X-ray tube housing 19. The light source 200 may be suitably shielded at 204.

Light refracting structure is located in the path of light transmitted from the source 200, such structure advantageously taking the form of a double prism 206 attached to the shield 204, for example, and extending in openly spaced confronting relation to the component 112. Light projected downwardly via iris 204a and in the prism, as rays 207 and 208 is reflected by prism face 209 as rays 207a and 208a, and an upper image 204b of the iris 204a in the shield may be formed between the rays 207a and 208a as for example on a patient's face. Similarly, light projected downwardly via the iris as rays 211 and 212 is reflected by prism face 210 as rays 211a and 212a and a lower image 204c of the iris may be formed between the rays 211a and 212a as on a patient's face. Images 204b and 204c delineate the upper and lower limits of a facial area in the main path 107 of the X-rays from the target. Accordingly, the technician will known precisely where to locate the X-ray film adjacent the patient's face.

Figure 18:
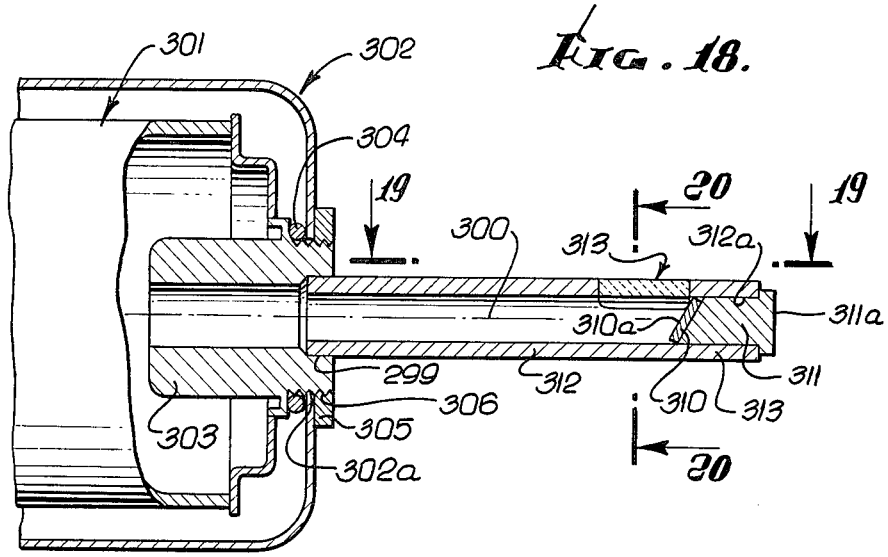
FIG. 18 is a side elevation view of further modified intra-oral X-ray tube apparatus.
Figure 19:
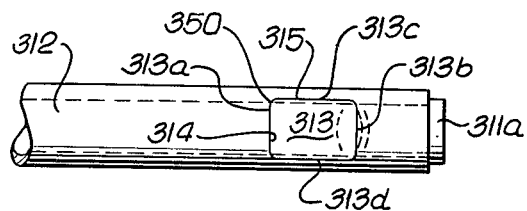
FIG. 19 is a top plan view on lines 19—19 of FIG. 18.
Figure 20:
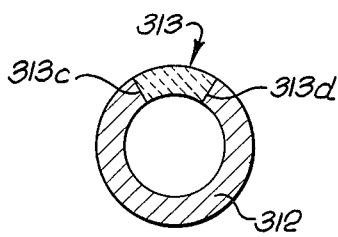
FIG. 20 is an end view on lines 20—20 of FIG. 18.

Referring now to FIGS. 18–20, the illustrated X-ray tube means for providing an electron beam along axis 300 includes an X-ray tube 301 contained within housing 302. The tube anode appears at 303, and the housing is attached to the anode as via O-ring 304 and nut 305 threaded on the anode at 306 to retain the housing bore portion 302a thereto.

A target for the beam is indicated at 310, and may consist of tungsten. Its surface 310a is angled to face forwardly and sidewardly, as shown, and it is supported by an electrically conductive part 311 located rearwardly thereof. Part 311 and the target are located within an elongated carrier 312 adapted to be received in the patient's mouth. The carrier defines a tubular X-ray shield, and for that purpose the tubular carrier may consist of copper. Part 311 is in electrical contact with the carrier at 313 for grounding of the target; thus, the part may fill carrier bore 312a. Head 311a fits against the end of the carrier to accurately position the target, axially. The carrier is connected to the anode 303 at 299.

A ceramic element is provided to define an X-ray window carried by the carrier and positioned to sidewardly laterally pass X-rays emanating from the target in response to electron beam impingement on the target.

In that form of the invention shown in FIGS. 18–20, the ceramic window 313 is located in a side-opening or cut-out 314 formed in tubular shield or carrier 312, and it may be peripherally brazed in position as shown at 315. The window is laterally arcuately curved to match the curvature of the tubular shield, and it has longitudinally spaced, laterally extending edges at 313a and 313b, as well as circularly spaced, longitudinally extending edges 313c and 313d. Such edges or boundaries define the shape of the cone of X-radiation passed by the window. Edge 313b laterally overlaps the target, as shown in FIG. 19. The use of a ceramic window is found to result in very clear, X-ray produced images of teeth, on film located as previously described. The window may be of uniform radial thickness.

Figure 21:
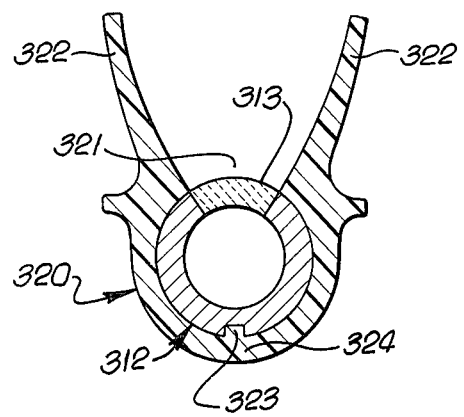
FIG. 21 is a view like FIG. 20, with a shield and tongue suppressor attachment.

FIG. 21 shows the X-ray shielding and tongue suppressor means 320 (corresponding to that described earlier at 112) carried by the shield 312, with a side opening 321 in lateral registration with window 313. Side opening 321 is formed between laterally diverging arms 322 having laterally diverging interior surfaces as shown. A keyway or other guide shoulders at 323 provide a longitudinal interfit between the carrier 312 and the base 324 of the attachable means 320 to assure proper lateral registration of opening 321 with the ceramic window. The ceramic window is thus a cylindrical segment having rounded corners at 350.

Figure 22:
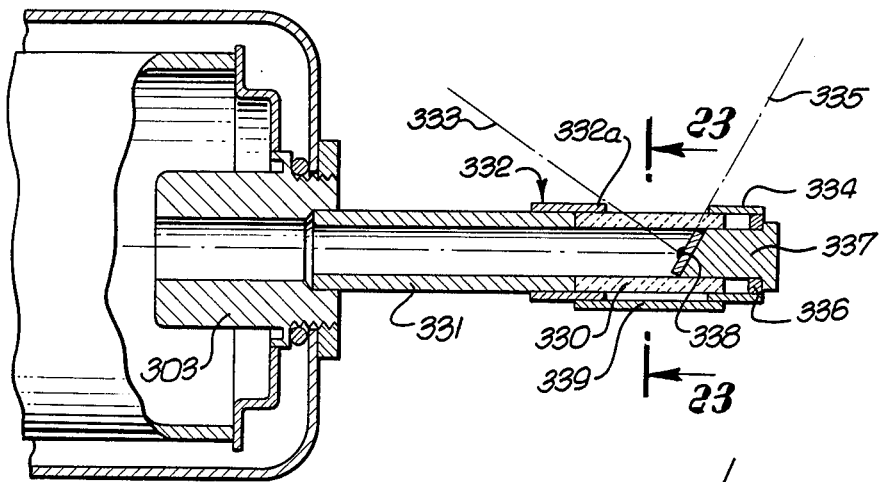
FIG. 22 is a side elevation showing still further modified intra-oral X-ray tube apparatus.
Figure 23:
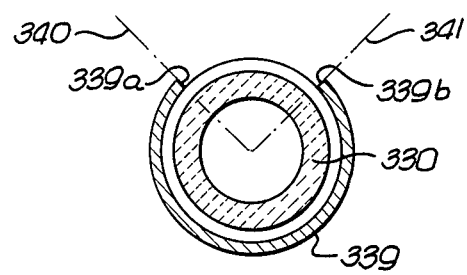
FIG. 23 is a section on lines 23—23 of FIG. 22.

Turning to FIGS. 22 and 23, the modified ceramic element 330 forms a complete cylinder and is held in coaxial end-to-end relation with the tubular shield or carrier 331, which may likewise consist of copper. For example, a thin metallic (nickel) sleeve 332 may extend closely about and position tubular portions of the shield 331 and ceramic element 330. In this case, the sleeve portion 332a overlapping the ceramic element defines an X-ray shield and a boundary of the window to limit the X-ray cone at locus 333. Another and like sleeve 334 fits over the opposite end portion of the ceramic element to limit the X-ray cone at 335. A metallic ring 336, as for example copper, fits within the sleeve 334 and is joined thereto in spaced relation to the ceramic element, and the electrically conducting support 337 for the target 338 is received within the ring 336 and the ceramic tube, as shown.

An auxiliary, semi-cylindrical X-ray shield 339 extends partly about ceramic element 330 and about the sleeves 332 and 334 to establish an electrically conductive grounding path between the target, part 337, sleeves 334 and 332, carrier tube 331 and the anode 303. Shield 339 has longitudinal edges 339a and 339b which establish boundaries 340 and 341 for X-rays passing through the window. The cone angle between the boundaries 340 and 341 is typically about 45°, whereas the cone angle between boundaries 333 and 335 is typically about 75°.

The shield 339 may consist of lead, and usable ceramic compositions for tube 330 and window 313 include the following examples, others being possible:

| I | | |
|---|---|---|
| beryllium oxide | about 90%, | by weight |
| silicon dioxide | about 7% | " |
| impurities | | |
| (clays, magnesium etc.) | balance | " |
| II | | |
| aluminum oxide | about 90% | " |
| silicon dioxide | about 7% | " |
| impurities (see above) | balance | " |

Figure 24:
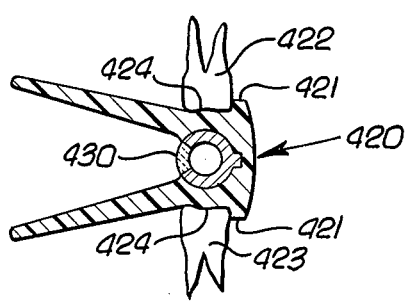
FIGS. 24 and 25 are views like FIG. 11, showing modified attachments.
Figure 25:
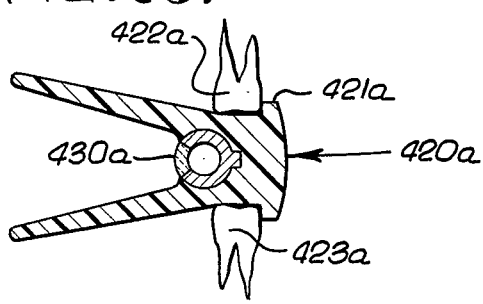

Referring to FIG. 24, it shows a ceramic tubular element 430, like element 330 in FIG. 22, onto which an element positioning, X-ray shielding, tongue suppressing means 420 is received. The means 420 corresponds to that described at 320 in FIG. 21, excepting that the ears or tabs 421 are located out of alignment with the tubular element 430. Molars 422 and 423 are in alignment with the tube, and are received in pockets 424 formed by the means 420. FIG. 25 is similar, excepting in this case, the tabs 421a on modified means 420a are sufficiently spaced from and at the outer side of the tube 430a that the latter is positioned at the inner sides of the molars 422a and 423a. Positioning of the tubes by the means 420 and 420a eliminates need for repetitive retaking of radiographs, reducing or eliminating aggravations and irritation of the patient.

Figure 26:
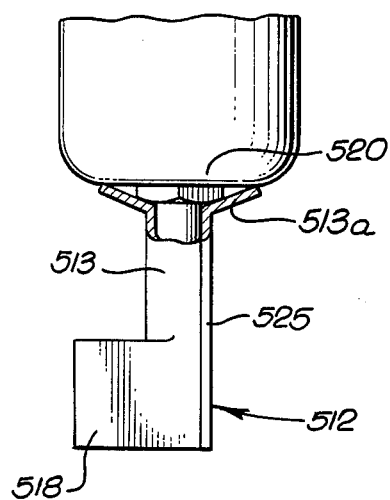
FIG. 26 is a view like FIG. 12, showing another modified attachment.

In FIG. 26 the tube positioning, X-ray shielding, tongue suppressing means 512 corresponds to means 112 of FIG. 10; however, stem 513 is annularly flared at its end 513a to fit over the end 520 of the tube housing. As a result, a patient's mouth does not come into contact with the tube or its housing, and the stem 513 acts as a sterile cover for the tube and housing. Elements 518 and 525 correspond to elements 118 and 125 in FIG. 10.

I claim:

1. In dental X-ray apparatus, the combination comprising
   a. X-ray tube means for providing an electron beam,
   b. a target for said beam, and
   c. a carrier for said target and locating the target in longitudinally spaced relation from said means to be received rearwardly into a patient's mouth,
   d. said carrier defining a tubular X-ray absorbing shield, and there being a ceramic element defining an X-ray window carried by the carrier and positioned to sidewardly laterally pass X-rays emanating from the target, said shield extending at the side of the target spaced from the window, the shield and target being integrally connected.

2. The apparatus of claim 1 including an electrically conductive part located in the carrier and supporting the target.

3. The combination of claim 1 wherein said ceramic element is cylindrical and extends in coaxial relation with the tubular shield.

4. The combination of claim 3 including an auxiliary, semicylindrical X-ray shield extending partly about the cylindrical ceramic element, certain boundaries for X-rays passing through the ceramic window defined by adjacent edges of the semicylindrical shield.

5. The combination of claim 3 including a metallic sleeve extending about and positioning portions of the ceramic element and of the tubular shield, said sleeve defining an X-ray shield and defining a boundary of the window.

6. The combination of claim 3 including an electrically conductive part located in the ceramic element and supporting the target therein.

7. The combination of claim 4 including an electrically conductive part located in the ceramic element and supporting the target therein, said auxiliary X-ray shield providing an electrically conductive path between said part and said carrier which is also electrically conductive.

8. The combination of claim 7 wherein said tubular shield consists essentially of copper, and said auxiliary shield consists essentially of lead.

9. The combination of claim 8 including a nickel sleeve extending about and positioning portions of the ceramic element of the tubular shield.

10. The combination of claim 1 wherein said window is located in a side opening formed in the tubular shield.

11. The combination of claim 10 including an electrically conductive part located in the carrier and supporting the target proximate the ceramic window.

12. The combination of claim 10 wherein the window has a periphery which is braze connected to the tubular shield.

13. The combination of claim 11 wherein the tubular shield is also electrically conductive and electrically connected with said part.

14. The combination of claim 13 wherein said part consists essentially of copper.

15. In dental X-ray apparatus, the combination comprising
   a. X-ray tube means for providing an electron beam,
   b. a target for said beam, and
   c. a carrier for said target and locating the target in longitudinally spaced relation from said means to be received rearwardly into a patient's mouth,
   d. said carrier defining a tubular X-ray shield, the shield and target being integrally interconnected, and there being a ceramic element defining an X-ray window carried by the carrier and positioned to sidewardly laterally pass X-rays emanating from the target,
   e. said shield and window having cylindrical surface extent, and including X-ray shielding and tongue suppressor means carried by the shield to be received into the patient's mouth, said means forming a side-opening in registration with said ceramic window, said means having arms having interior surfaces which diverge sidewardly away from said opening, said arms projecting sidewardly away from said carrier.

16. The combination of claim 15 wherein said tongue suppressor means includes structure integral with said arms and engageable with a patient's teeth to align the carrier and target relative to X-ray film, whereby need for repetitive re-taking of radiographs is eliminated and coning of the X-ray beam relative to the film is provided by said arms.

17. The method of using an elongated tubular carrier containing an X-ray beam target, the carrier having a side window to pass X-rays emanating from the target, there being means to direct an electron beam in the carrier at the target, and there being a tube positioning and X-ray beam coning attachment on the carrier, that includes
   a. locating the carrier and target outside of a patient's mouth to direct X-rays through facial tissue and through teeth toward film,
   b. attaching the attachment to the carrier,
   c. inserting the carrier and attachment into the patient's mouth into a position for clenching of the attachment by the patient's molars, and then employing the carrier and target to direct X-rays panoramically through patient's teeth and toward another film.

* * * * *